United States Patent [19]

Bailey

[11] 4,053,388
[45] Oct. 11, 1977

[54] PROCESS FOR PREPARING AROMATICS FROM NAPHTHA

[75] Inventor: Angus B. Bailey, Dallas, Tex.

[73] Assignee: Moore-McCormack Energy, Inc., Dallas, Tex.

[21] Appl. No.: 747,863

[22] Filed: Dec. 6, 1976

[51] Int. Cl.$^2$ .................. C10G 23/00; C10G 34/00
[52] U.S. Cl. ............................. 208/89; 260/672 T
[58] Field of Search ............... 208/89, 62; 260/672 T

[56] References Cited

U.S. PATENT DOCUMENTS

| | | | |
|---|---|---|---|
| 3,105,811 | 10/1963 | Engel | 208/89 |
| 3,192,150 | 6/1965 | Taylor et al. | 208/62 |
| 3,542,667 | 11/1970 | McMahon et al. | 208/62 |
| 3,714,023 | 1/1973 | Stine | 208/62 |
| 3,927,135 | 12/1975 | Suggitt et al. | 260/672 T |

Primary Examiner—George Crasanakis
Attorney, Agent, or Firm—Kenyon & Kenyon, Reilly, Carr & Chapin

[57] ABSTRACT

This invention is directed to producing a high yield of aromatics from naphtha by integrating a catalytic reformer and a thermal hydrocracking unit followed by fractionating the product stream to obtain the desired aromatic. In this process, after sulfur is removed, the naphtha is catalytically reformed under conditions adapted to provide the maximum aromatic content. The reformed stream is then thermally hydrocracked, preferably in a system containing multiple reactors. The process does not require an external source of hydrogen since the reforming and hydrocracking units are operated to maintain a hydrogen balance. The hydrocracked stream is fractionated in a series of columns to produce the desired mix of aromatics. In one example, the fractionation separates out (1) benzene, which is further purified, if necessary (2) a toluene stream and a C$_9$+ aromatic stream which are charged to a transalkylation reactor to produce a composition containing mixed xylenes sent to recycle and (3) a mixed xylene stream from which paraxylene is separated by a liquid-solid adsorption technique and from which the remaining xylenes are isomerized to produce further paraxylene. A by-product stream of light hydrocarbons is also produced. This procedure can be readily modified to produce greater amounts of benzene and/or toluene and less xylene.

15 Claims, 3 Drawing Figures

PROCESS FOR PREPARING AROMATICS FROM NAPHTHA

BACKGROUND OF THE INVENTION

In the reforming of naphtha to produce high quality gasoline substantial amounts of mixed aromatics are produced, particularly benzene-toluene-xylenes and ethylbenzene. An approach which has been tried for the production of aromatics, primarily a substantially pure stream of benzene from naphtha, is set forth in British Pat. No. 1,157,114. This patent discloses the integration of a reforming unit and a thermal hydrocracking unit for producing predominantly benzene and a fuel gas from naphtha. In a first stage endothermic reaction, a naphtha and hydrogen stream are reacted at about 500 psig in a catalytic reforming operation to produce aromatic compounds from paraffins, olefins and cyclic hydrocarbons. In a second stage exothermic reaction at about the same pressure, the reformate stream is subjected to thermal hydrocracking to produce methane and ethane from paraffins, and to dealkylate aromatic compounds. Steam and/or sulfur is added to prevent coking in the thermal hydrogenation reactor. The principal product stream of this process is a mixture of about 75% benzene, 14% toluene and 7.5% xylene which is then further treated to produce substantially pure benzene, a toluene-rich stream of benzene-toluene-xylene, and a xylene-rich stream containing higher aromatics. The second major product stream is a fuel gas rich in methane, ethane, hydrogen, carbon monoxide and carbon dioxide, and containing sulfur compounds. Although a hydrogen recycle stream may be used, an outside source of hydrogen is required to carry out the processes of this patent.

It is an object of this invention to provide an improved process for producing aromatics from naphtha. For example, it would be desirable to obtain a more efficient economical conversion of naphtha to aromatics such as benzene, toluene, and xylenes and to do so without an outside source of hydrogen.

It also would be desirable to upgrade in value the products of the foregoing process by increasing the xylene, and particularly the paraxylene content for use as a feedstock for the production of terephthalic acid or dimethylterephthalate. Furthermore, it is desirable to increase the available ethane, which as a feedstock for the production of ethylene has a higher value than methane.

Of the normal amount of mixed benzene-toluene-xylenes production, the minor proportion of the xylenes are recovered, for use as solvents and for chemical uses such as the production of terephthalic acid from paraxylene. The $C_8$ aromatics found in catalytic reformate generally occur in the following ratio

|  | Typical % | Range % |
| --- | --- | --- |
| Orthoxylene | 23 | 23-26 |
| Metaxylene | 40 | 35-40 |
| Paraxylene | 17 | 16-20 |
| Ethylbenzene | 20 | 17-21 |

The total amount of these aromatics in the reformate can be about 15 to 18%, although the amount can vary significantly depending upon the character of the feedstock and the processing conditions. However, even when a catalytic reformer is operated under conditions to maximize the production of benzene-toluene-xylenes further substantial efforts and additional costs are necessary to separate the components of this mixture and to produce a high-purity paraxylene. The paraxylene separation is usually carried out by crystallization or adsorption and the higher the content of paraxylene, the higher the value of the $C_8$ aromatic fraction. It is therefore preferable to seek first to increase the ratio and amount of xylenes in the product stream by chemical processing steps.

It is therefore a further object of this invention to produce a substantial yield of high purity paraxylene from a relatively wide cut, low quality naphtha. In addition, it is desirable to produce in this process nitration grade benzene, pipe line quality gas high in ethane, propane, and small quantities of higher boiling paraffin compounds.

Another object of this invention is to carry out hydrodealkylation of the effluent from a catalytic reformer operated on high end point naphthas so that the effluent contains $C_9$, $C_{10}$ and $C_{11}$ aromatics, making it possible to:

increase the total aromatic content of the effluent to produce and recover as much as 62%, or more, aromatics from an Arabian naphtha;

minimize the formation of methane in the gas produced, and maximizing the ethane content;

hydrocrack substantially all of the paraffins in the effluent to methane, ethane, and propane without the need for hydrogen beyond that produced in the reformer;

produce a mixed xylene fraction with an enhanced paraxylene content; and accomplish the foregoing through processing techniques that reduce investment and operating costs substantially below conventional methods.

Other objects will be set forth in the following detailed description of the invention.

SUMMARY OF THE INVENTION

This invention is directed to a process for treating naphtha to produce a substantial amount of aromatic compounds such as benzene, toluene and xylene. The invention will be explained primarily by setting forth a process for the production of paraxylene and by-product streams of benzene, propane and fuel gas. As set forth below, this process can be readily modified to make greater quantities of benzene and/or toluene with concommitantly lower amounts of xylenes.

The process steps for making paraxylene include naphtha pretreatment, catalytic reforming, thermal hydrocracking, gas recovery, aromatics fractionation, aromatics transalkylation, paraxylene recovery and xylenes isomerization. A heavy naphtha, having a boiling point range of about 212° F to 374° F, is initially desulfurized by hydrogen treatment and other impurities are removed to prevent catalyst poisoning in subsequent steps.

The treated product stream is passed through a series of reforming reactors and then directly to a thermal hydrocracking reactor. These reactors are substantially in hydrogen balance so that an external source of hydrogen is unnecessary. The reformer is operated at a low-pressure and high severity to promote the formation of aromatics from paraffins. The thermal hydrocracking reactor is operated to convert most of the heavier paraffins to lighter paraffins and the heavy aromatics are partially demethylated. The rate of the hydrocracking or dealkylation reaction increases with the molecular weight of the aromatics so that this reaction can be controlled to substantially increase the concentration of toluene and xylene.

The hydrocracking reactor outlet is cooled and separated into liquid and gas streams. By-product hydrogen and other gases are recovered by treatment through a compressor, absorber and cryogenic unit. The hydrogen is used in the several recycle streams in the process, primarily in the reformer and hydrocracking unit. The other gases which are separated may be used for fuel or subjected to further separation techniques for conversion to other products. The liquid product stream is optionally treated in a stabilizer to remove propane and other gases.

The major product stream then passes through a deisohexanizer from which paraffins are recovered overhead. The bottoms product stream and recycle production from downstream operations are passed through a series of distillation columns to separate the aromatic compounds. The first tower produces overhead a benzene stream which may contain some paraffins and other compounds. Depending on the amount, if any, of paraffins the benzene may be charged to an extractive distillation tower which recovers pure benzene and a by-product paraffin stream which may be used for fuel. The bottoms from this benzene tower are charged to the next tower from which toluene is removed overhead for use downstream in a transalkylation unit. The toluene tower bottoms are charged to the next tower from which mixed xylenes are removed overhead and sent to a paraxylene recovery operation. The xylene tower bottoms go to a rerun column from which an overhead $C_9^+$ stream is recovered for use in the transalkylation unit. The rerun column bottoms are heavy aromatics which may be used as fuel or partially recycled.

Alternatively, the xylene tower bottoms may be recycled to the thermal hydrocracking reactor and the transalkylation process eliminated from the processing sequence. The toluene bottoms can be used as a final product or converted to benzene — if additional xylenes are not desired.

The transalkylation unit produces mixed xylenes from a mixture of higher and lower aromatics. The overhead from the rerun column and toluene column and some of the bottoms from the xylene column are charged to the transalkylation unit. A catalytic transfer of methyl groups occurs to produce an equilibrium mixture of xylenes, benzene, and some heavier aromatics. The liquid product is recycled to the aromatics fractionation section and the gas output can be used for fuel.

A paraxylene adsorption recovery unit is used to separate paraxylene from the mixed xylenes obtained from the overhead of the xylene column. Paraxylene is recovered by adsorption from the liquid phase in a fixed bed of solid adsorbent. The alternative method commercially used is a low-temperature crystallization process to separate paraxylene.

A xylene isomerization unit is used to prepare an equilibrium mixture of xylenes from the remaining by-product xylenes of the paraxylene recovery unit. These remaining xylenes (mainly metaxylene) are catalytically isomerized to a mixture of orthoxylene, metaxylene, and paraxylene, which is then recycled to the aromatics fractionation columns. Paraxylene comprises about 25% of the mixed xylenes obtained by isomerization.

The invention will be explained in greater detail in connection with a description of the attached Figures, and the embodiment of a typical run, based on computer derived standard operating conditions.

THE INVENTION

Arabian light crude oil may be chosen as the feedstock for this process. A large volume of it is readily available, its properties are well known, and naphthas cut from it are less suitable for other uses because of relatively poor catalytic reforming characteristics. Of course, naphthas from other crude oils may also be used.

The boiling range of the naphtha to be processed can be chosen from many available cuts. A wide boiling range naphtha (e.g. 160° to 400° F) may be used in this invention as opposed to conventional low end point narrow boiling range naptha used for benzene-toluene-xylene operations which restricts feedstock availability and increases naptha costs. Since hexanes and heptanes are difficult to convert and contribute little to the yield of paraxylene it is advantageous to substantially eliminate this fraction from the front end. The end point can be chosen to eliminate some $C_{12}$ and heavier aromatics in order to simplify side effects. A naphtha boiling range of 212° to 374° F is a preferred range.

Table I sets forth a typical set of properties, and is the charge stock used for the embodiment of this invention as set forth in the series of tables which follows.

TABLE I
CHARGE STOCK PROPERTIES

° API - 56.9
Boiling Range ° F 212/374
Crude Source: Arabian Light
Yield Cut Range Volume % Crude: 11.2 – 27.6
Yield on Crude Volume % 16.4
Total Sulfur, Weight % .032

FEEDSTOCK COMPONENTS

| Naphthenes | | Vol. % |
|---|---|---|
| $C_6$ | | 0.6 |
| $C_7$ | | 2.1 |
| $C_8$ | | 3.7 |
| $C_9$ | | 4.4 |
| $C_{10}$ | | 4.6 |
| $C_{11}$ | | 4.7 |
| | TOTAL | 20.1 |
| Aromatics | | |
| Toluene | | 1.8 |
| Ethyl Benzene | | 0.6 |
| O-Xylene | | 1.7 |
| M & P Xylene | | 2.2 |
| $C_8$ Aromatics | | 4.5 |
| $C_9$ Aromatics | | 4.4 |
| $C_{10}$ | | 4.4 |
| $C_{11}$ | | 1.6 |
| | TOTAL | 16.7 |
| Paraffins | | 63.2 |
| | TOTAL | 100.0 |

Charge: 20,000 BPSD

Figure 1:
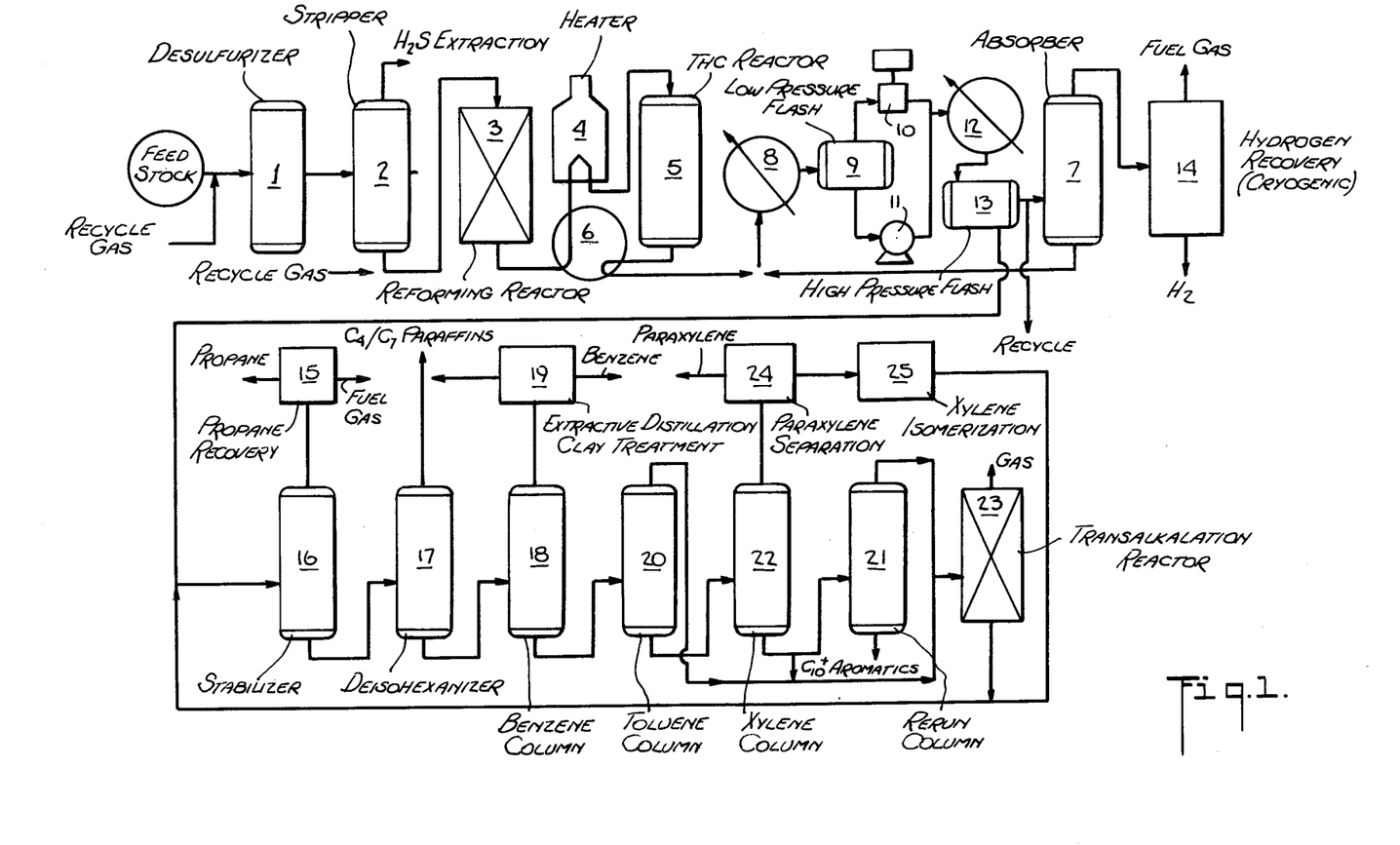
FIG. 1 is a schematic diagram showing the major operating steps and units for the present invention.

The naphtha is first mixed with a hydrogen-rich recycle stream, in a mol ratio of about 1:2 – 7 under a pressure of about 400 to 600 psi, preheated to about 650°–750° F, and passed over a conventional desulfurization catalyst (i.e. cobalt molybdenum or nickel molybdenum) in reactor 1 for the removal of sulfur and other contaminants which may be injurious to the catalytic reforming catalyst. The treated naphtha is cooled to about 120° F, recycle gas and liquid separated and the light ends (such as butane and lighter) are removed in a stripper tower 2. A tail gas containing the hydrogen sulfide is extracted in the stripper. The tail gas is treated in a conventional manner (not shown) to remove the H₂S in an amine unit after which the H₂S is then converted to elemental sulfur and the tail gas is treated in a hydrogen recovery unit for use in the recycle stream.

The treated naphtha is mixed with a hydrogen-rich recycle gas, preheated and charged to a semi-regenerative type reformer 3 (one or more stages, preferably three stages with interstage heating — not shown), operated at severe conditions chosen to give a six months cycle. The operation of this unit is adapted to ensure the information and retention of the maximum number of aromatics rings. Table II sets forth typical conditions for a 'Rhenforming' catalytic reforming useful in this invention.

TABLE II

| Process Conditions | Ex. I | Ex. II |
|---|---|---|
| LHSV hr $^{-1}$ | 0.88 | 1.06 |
| H₂/HC mol/mol | 6.0 | 6.0 |
| PSIG-Reactor outlet | 200 | 275 |
| C₅ + Octane | 102 | 102 |
| Run length-months | 5½ | 6.0 |
| ° F (Start of Run) | 955 | 970 |
| Max ° F (End of Run) | 1025 | 1025 |

Rhenforming is one of a number of commercially used catalytic reforming processes; it employs platinum-ruthenium catalyst which was the basis for the data of Table II in which the catalyst was Type E (see The Oil and Gas Journal, pp. 121–130 (May 1, 1976)). This process may be carried out at pressures from about 125 to 275 psig and at average reaction temperatures of about 900° to 1100° F, preferably about 955° to 1025° F, with a liquid hourly space velocity of about 0.7 to 3.1, preferably about 0.8 to 1.1 and a molar ratio of hydrogen to hydrocarbons of about 3 to 11, preferably about 5 to 7.

Table III sets forth typical reformer yield estimates for the process of this invention. In this and subsequent tables, the prefix N is for normal (or straight-chain hydrocarbons), and I is for iso (or branched-chain hydrocarbons). The suffix P is for paraffin, N is for naphthene and A is for aromatic. The abbreviation Bz is for benzene, T for toluene, EB for ethyl benzene, Px for paraxylene, Ox for orthoxylene and Mx for metaxylene. The data is based upon the charge stock of Table I.

TABLE III
CATALYTIC REFORMER NET PRODUCT YIELDS

| | Vol. % | B/D | Wt. % | #/Hr. | Mols/Hr. |
|---|---|---|---|---|---|
| H₂ | | | 2.89 | 6,325 | 3,137.4 |
| C₁ | | | 1.19 | 2,604 | 162.7 |
| C₂ | | | 2.23 | 4,880 | 162.1 |
| C₃ | | | 3.00 | 6,566 | 148.8 |
| IC₄ | 1.94 | 388 | 1.44 | 3,152 | 54.3 |
| NC₄ | 2.81 | 562 | 2.17 | 4,749 | 81.7 |
| IC₅ | 3.00 | 600 | 2.47 | 5,406 | 75.0 |
| NC₅ | 1.98 | 396 | 1.65 | 3,611 | 50.0 |
| C6P | 6.37 | 1,275 | | 12,349 | 143.3 |
| C7P | 3.97 | 795 | | 7,999 | 79.8 |
| C8P | 1.00 | 200 | | 2,039 | 17.9 |
| C9P+ | 1.40 | 280 | | 2,659 | 20.8 |
| C6N | .10 | 20 | | 218 | 2.6 |
| C7N | .40 | 80 | | 932 | 9.5 |
| C8N+ | .20 | 40 | | 474 | 4.2 |
| Bz | .50 | 100 | | 1,288 | 16.5 |
| T | 6.20 | 1,240 | | 15,754 | 171.0 |
| EB | 3.47 | 694 | | 8,817 | 83.0 |
| px | 4.16 | 832 | | 10,498 | 99.0 |
| m-x | 9.70 | 1,940 | | 24,580 | 231.4 |
| o-x | 5.78 | 1,156 | | 14,910 | 140.4 |
| C₉A | 20.15 | 4,030 | | 51,418 | 427.8 |
| C₁₀A | 9.30 | 1,860 | | 23,471 | 174.9 |
| C₁₁A | 1.55 | 310 | | 3,858 | 26.0 |
| TOTAL | 83.99 | 16,798 | | 218,557 | 5,520.1 |

The effluent from the last reactor of the catalytic reforming unit passes directly through a heat exchanger 6 and then through start-up heater 4 and into a thermal hydrocracking reactor 5 which operates at a pressure range between 125 to 275, or up to 375 psig. In the illustrated procedure the pressure was 180 psig and the outlet temperature was maintained below about 1350° F. The reaction in this reactor is exothermic but carefully controlled by mixing with feed and recycle hydrogen which normally eliminate the need for any other quench. The residence time in the thermal hydrocracking unit is short and with the low pressure and temperature the degree of reaction is held to a level where a heat balance is maintained. This operation is adapted to convert aromatic compounds containing 9, 10, and 11 carbon atoms into benzene, toluene, and xylenes thereby:

1. increasing the total xylenes produced from the naphtha feed;
2. adjusting the ratio of toluene to C₉ plus aromatics to nearly an equal molar ratio so that maximum xylenes may be produced by transalkylation;
3. substantially reducing or eliminating all paraffins boiling in the xylene boiling range. This reduces the additional demands that would otherwise be placed on the xylene isomerization catalyst and reduces the size of the paraxylene extraction unit and xylene isomerization units and reduces their operating cost. This approach is more economical than solvent extraction of the C₈ fraction which also leads to loss of some aromatics to the raffinate;
4. converting high boiling paraffins into methane and ethane and propane which have a higher monetary value per unit heating value;
5. reducing the paraffin content of the benzene cut thereby making possible the production of benzene of nitration grade by fractionation or by extractive distillation at lower cost than by liquid/liquid solvent extraction;
6. converting some paraffins and isoparaffins into aromatics at the operating pressure proposed. Process yields presented below do not take this reaction into account but would improve the yield by several percent; and
7. converting indan into benzene and light hydrocarbons. While only about 2% of the C₉ fraction from catalytic reforming is indan, it is a catalyst poison to the transalkylation reaction. Although modest amounts of indan may be tolerated in the combined feed to the transalkylation unit, some compensation in operating conditions is required such as temperature compensation to offset depression of catalyst activity. The C₉ cut is usually fractionated to remove most indan. This requires rejection of some trimethylbenzene to the indan fraction, ultimately reducing paraxylene yields, and also requires high investment in a C₉ fraction splitter and associated high operating costs. By use of the thermal hydrogenation reactor, indan is reduced to levels such that a splitter is not required. The transalkylation unit may still require a rerun column to remove heavy aromatics formed during the reaction but this is a much smaller less precise column.

Table IV sets forth typical thermal hydrocracking yield estimates for the process of this invention.

TABLE IV
THERMAL HYDROCRACKING

| Reactor | Mols/Hr. In | Out | Recycle | Net Out | Net Out Lbs./Hr |
|---|---|---|---|---|---|
| $H_2$ | 13,238.4 | 11,538.7 | 10,101.0 | 1,437.7 | 2,898 |
| $C_1$ | 1,757.7 | 3,149.5 | 1,595.0 | 1,554.5 | 24,872 |
| $C_2$ | 1,757.1 | 2,192.9 | 1,595.0 | 597.9 | 17,997 |
| $C_3$ | 348.8 | 497.1 | 200.0 | 297.1 | 13,102 |
| $C_4$ | 136.0 | 174.3 | | 174.3 | 10,127 |
| $C_5$ | 125.0 | 61.0 | | 61.0 | 4,398 |
| $C_6$ Saturates | 145.9 | 22.0 | | 22.0 | 1,896 |
| $C_7$ Saturates | 89.3 | 4.8 | | 4.8 | 481 |
| $C_8$ Saturates | 22.1 | 0.7 | | 0.7 | 80 |
| $C_9$ Saturates | 20.8 | 0.2 | | 0.2 | 26 |
| Benzene | 16.5 | 67.7 | | 67.7 | 5,287 |
| Toluene | 171.0 | 350.3 | | 350.3 | 32,260 |
| $C_8A$ | 553.7 | 671.6 | | | |
| EB | | | | 100.7 | 10,694 |
| px | | | | 120.1 | 12,755 |
| mx | | | | 280.6 | 29,800 |
| ox | | | | 170.2 | 18,075 |
| $C_9A$ | 427.8 | 272.4 | | 272.4 | 32,742 |
| $C_{10}A$ | 174.9 | 7.4 | | 7.4 | 993 |
| $C_{11}A$ | 26.0 | 0.5 | | 0.5 | 74 |
| TOTAL | | | | 5,520.1 | 218,557 |

The conventional thermal hydrocracking operation in commercial operation is the hydrodealkylation of toluene to benzene and methane. The toluene is produced by using a solvent to extract aromatics from a fractionated reformate and by then fractionating the extracted aromatics to obtain toluene. Toluene is a relatively stable compound and requires severe conditions for the reaction to proceed and to obtain a reasonably high conversion per pass to benzene. For example to convert 75% of toluene per pass through the reactor, the conditions in a commercial unit may be:

| | |
|---|---|
| Reactor pressure | 600 psig |
| Inlet temperature | 1,200° F |
| Outlet temperature | 1,360° F |
| $H_2$/toluene at inlet | 7/1 mol/mol |
| Reactor residence time | 25 seconds |

Time and temperature are to some degree interchangeable, with lower temperatures and longer time giving equal conversions. A high hydrogen pressure is necessary to suppress the formation of coke at the high temperatures and long residence times used for toluene dealkylation. Higher pressure also reduces the size of the reactor required for a given residence time. Higher pressures may also increase the rate of dealkylation.

By reducing the thermal hydrogenator reactor pressure, the synthesis of aromatics from paraffin and naphthene hydrocarbons increases. This is the reaction sought in the catalytic reforming process. In the reforming process the conversion of paraffins and cycloparaffins to aromatics is enhanced at reduced pressures. Low pressures also favor increased hydrogen production in reformers. A few years ago most reformers operated around 500 psig to reduce deactivation of the platinum catalyst due to fouling. The recent development of more stable catalyst has permitted reformers to operate at reduced pressures, i.e. 200 psig or less.

In the present invention, after maximum conversion has been obtained in a catalytic reformer, still further conversion of paraffins to aromatics is obtained by charging the reformer effluent to a thermal hydrocracking reactor operated at low pressure and low $H_2$/oil ratio. Thus while few aromatics would be synthesized from paraffins at 600 psig in conventional hydrodealkylation, appreciable synthesis can occur at selected controlled conditions.

Another effect of reducing pressure is the production of increased amounts of ethane. The rate of thermal hydrocracking of paraffins increases with the length of the carbon to carbon chain, with ethane being the most thermally stable. At 1,360° F and 25 seconds and 600 psig, most of the ethane will react to form methane, and ethane will be less than 25 mol % of the total methane and ethane produced. By reducing the temperature to 1,300° F, the pressure to 200 psig or less, and reducing the residence time, ethane and methane can be produced in almost equal molar percents. Reducing the $H_2$/oil ratio further substantially increases the percentage of ethane produced.

Operations of a thermal hydrocracking reactor at 200 psig pressure and 1,300° F and a short residence time will give a low rate of toluene dealkylation to benzene. Dealkylation of higher aromatics proceeds much more rapidly than toluene. The dealkylation rates of various aromatics relative to toluene are set forth below. (The data in parenthesis is from Betts, Popper, Silsby — Journal of Applied Chemistry, 7, 497 (1957)).

| Aromatics | Relative Ratio |
|---|---|
| Toluene | 1 |
| Ethylbenzene | 2.2 |
| Paraxylene | 2.4 (2.9) |
| Metaxylene | 2.6 (3.5) |
| Orthoxylene | 4.6 (6.3) |
| $C_8$ Aromatics as group | 2.7 |
| $C_9$ Aromatics as group | 4.4 |
| $C_{10}$ Aromatics as group | 10.0 |
| $C_{11}$ Aromatics as group | 17.6 |

When $C_8$ or heavier alkyl benzenes are present in feeds there is a very large increase in the rate of toluene dealkylation over cases in which toluene along is present. All of the dealkylation reaction rates are apparently increased so less severe conditions may be employed with mixtures than with pure toluene. The higher reaction rates which occur when hydrodealkylating mixtures of aromatics over those experienced in dealkylating toluene alone permits the use of much smaller, less expensive reactors than would be required if the rate accelerating effect of mixtures were not considered in the reactor design.

It is the purpose of the present process to operate at those conditions which will dealkylate $C_9$ and heavier aromatics to $C_8$ and lighter. At these conditions some $C_8$ aromatics will also dealkylate, but a higher percentage of $C_9$ aromatics will be dealkylated so the percentage yield of mixed xylenes will increase. Since orthoxylene and metaxylene dealkylate at a faster rate than paraxylene, the concentration of paraxylene in the $C_8$ fraction will increase. These same conditions will also favor the production of additional aromatics from paraffins and the production and retention of ethane in lieu of methane to a considerable degree. Substantially lower volumes of hydrogen are consumed in producing ethane and xylenes versus methane and benzene from a catalytic reformer effluent. Hydrogen requirements for the thermal hydrogenation reactor are therefore below the volumes produced in the catalytic reformer.

Operation of the reforming unit results in the net production of hydrogen which is substantially consumed in the thermal hydrocracking unit under the conditions set forth. By controlling the degree of hydrocracking, it is possible to ensure that the amount of available hydrogen produced in the reformer is sufficient for continuous operation, and thus an external source of hydrogen is not required. The product stream most readily controlled in accordance with available hydrogen is the butane/heptane fraction taken off downstream from the thermal hydrocracking reactor. This fraction can be processed closer to extinction by conversion with lighter hydrocarbons with adequate hydrogen. Conversely, greater amounts are produced as a by-product when sufficient hydrogen is not available.

Suitable conditions for the thermal hydrocracking reaction includes pressures of from about 125 to 275, or up to 375 psig and temperatures from about 1200° to 1380° F and residence times from about 5 to 8 seconds. Recycle hydrogen may be added as discussed below. The thermal hydrocracking reactor may be replaced by a catalytic unit which operates at a lower temperature but is more difficult to maintain.

The effluent from the thermal hydrocracking reactor passes through heat exchanger 6 and is mixed with rich oil from the absorber 7. After passing through coolers 8 the mixture flows to the low pressure flash drum 9. The vapors from the drum are compressed in 10, mixed with liquid pumped in 11 from the drum 9, cooled in 12, and flashed in 13 at a higher pressure. About half of the gas from drum 13 is recycled to reformer and the remainder of the net product gas is passed through an absorber 7 (and optionally a molecular sieve), and into the low temperature hydrogen recovery unit 14. The net product gas from the cryogenic separator 14 contains not over 5% by volume hydrogen and is compressed and may be sold as pipe line quality fuel gas or further processed for chemical uses. The hydrogen rich vapor is used in desulfurization of the naphtha feedstock and as recycle to the catalytic reformer and as quench if needed in the THC reactor. Each of the major components separated as overhead from the absorber may be recovered separately. Thus as the absorber overhead product is cooled, liquid ethane can be separated and as the temperature is reduced further liquid methane can be recovered.

The advantages of this process are illustrated in Table V by comparing the composition of the liquid flowing from the high pressure flash drum 13 to the stabilizer 16, produced from a 374° F EP naphtha in accordance with this invention, with the composition of a reformate from a 310° F naphtha from the same crude source. The 310° F naphtha yields were produced at the severe condition of 125 psig to produce the maximum aromatic content for this naphtha versus the less severe condition of 200 psig for the 374° F EP.

TABLE V

| Aromatic Content | | | |
|---|---|---|---|
| LV% of feed | | 374° F EP | 310° F EP |
| Benzene | | 2.1 | 5.1 |
| Toluene | | 12.7 | 15.1 |
| $C_8$ Aromatics | | 28.1 | 18.1 |
| $C_9$ Aromatics | | 12.8 | 7.4 |
| $C_{10}+$ Aromatics | | 0.4 | 0.4 |
| | TOTAL | 56.0 | 46.1 |
| $C_5+$ Paraffin & Naphthene | | 3.7 | 32.0 |

More than 70% of the 3.7% of $C_5+$ paraffins and naphthene consists of molecules having five and six carbon atoms which will be recovered as overhead products in the stabilizer and deisohexanizer. The $C_8$ aromatics constitute 50% of the total aromatics produced from the 374° F EP naphtha but only 39% from the 310° F EP. Also the potential for additional $C_8$ aromatics by disproportionation or transalkylation is much higher with the 374° F EP than with the 310° F EP. Less energy has been expended to this point in the process of the invention than in a conventional reforming unit because the exothermic heat of thermal hydrocracking has partially offset the endothermic heat of reforming. Further the composition of the liquid at this point makes downstream processing much easier and less expensive (i.e. reduced paraffin, indan, ethyl benzene content).

Liquid from the high pressure flash drum 13 flows to a stabilizing (depentanizing) column 16, a deisohexanizing column 17, and thence to a benzene fractionating column 18. The stabilizer separates light hydrocarbons overhead which pass to a propane recovery unit 15 from which propane and a salable fuel gas are obtained. The stabilizer 16 can be eliminated if desired to reduce capital expenditure, in which case propane and other light hydrocarbons can be taken overhead from the deisohexanizer 17. Of course, it is also possible to incorporate additional units or eliminate other units in the fractionation chain by incorporating a function or step in other more carefully controlled units or by eliminating a function or step to produce a less carefully cut product fraction. Alternatively, the flow pattern depicted can in effect be reversed by taking off the heavier or higher boiling components first and sending the remainder downstream for further fractionation.

A portion of the bottoms product from the deisohexanizer can be recycled to the absorber 7 to assist in the separation of fractions in that unit and particularly to help break the entrapment of any benzene in the product stream to overhead.

The overhead from the fractionating column 18 is a benzene concentrate which, if necessary for very high purity, may be processed in an extractive distillation unit 19, such as a Lurgi Distapex, for the production of nitration grade benzene and a small quantity of raffinate which is combined with the overhead from the deisohexanizer to provide a $C_4/C_7$ paraffin by-product stream. Table VI sets forth typical yield estimates for the extractive distillation unit.

TABLE VI

| EXTRACTIVE DISTILLATION YIELDS | | |
|---|---|---|
| Charge | B/D | #/Hr. |
| $C_6$ Saturates | | 1,896 |
| $C_7$ Saturates | | 481 |
| Benzene from Thermal Hydrocracking (THC) | | 5,287 |
| Benzene from Transalkylation (TA) | | 5,693 |
| Benzene from Isomerization | | 3,209 |
| TOTAL | | 16,566 |
| Yield | | |
| $C_6/C_7$ | 242 | 2,377 |
| Benzene | 1,101 | 14,189 |
| TOTAL | | 16,566 |

Either the deisohexanizer overhead or the raffinate from the benzene extractive distillation or both may be recycled to the thermal hydrocracking reactor for the production of additional methane and ethane to the extent of hydrogen availability. The bottoms from the benzene fractionating column are pumped to the toluene column 20.

The overhead cut from the toluene column is combined with the $C_9$ aromatics cut overhead from the rerun column 21 and a portion of the bottom cut from the xylene column 22 and charged to the transalkylation unit 23. This unit produces primarily xylenes in an equilibrium mixture but also some benzene, small amounts of ethyl benzene, and light paraffins.

The transalkylation reaction includes converting $C_7$ and $C_9$ (and higher) aromatics to $C_6$ and $C_8$ (with some $C_{10}$ and heavier). For example, toluene is passed over a fixed bed of catalyst to induce methyl group migration which leads to methylation and demethylation. Depending on the type of catalyst used, hydrogen gas may be present to depress coke formation. There is little ring destruction or hydrodealkylation, and thus minimal hydrogen consumption. Conversion of the toluene to benzene and xylenes is about 40% generally, although higher conversion is attainable along with increased side reactions. When the $C_9$ and heavier fraction is recycled in equilibrium amounts, benzene and xylenes are obtained in virtually equimolar ratio and in close to stoichiometric yields. The reaction is an equilibrium system and the composition of the product mix depends on the methyl/phenyl ratio in the feed, and thus use of increased amounts of $C_9$ aromatics increases the amount of xylenes produced.

Through the transfer of methyl groups, part of the feed is converted to mixed xylenes. Gas, benzene, heavy aromatics and some coke on catatlyst are also produced. The catalyst is regenerated by burning off the coke deposit. The gas and liquid streams, primarily for recycle, are separated in a flash drum which is part of the transalkylation.

The transalkylation reactor effluent, after heat exchange, flows to the stabilizer and fractionating train. Bottoms from the rerun column may be charged to the thermal hydrocracking reactor and/or used for fuel. Table VII sets forth typical yield estimates for the transalkylation unit.

TABLE VII

TRANSALKYLATION YIELDS

| Charge | Vol. % | B/D | Mols/Hr. | Lbs./Hr. |
|---|---|---|---|---|
| Toluene | 48.9 | 2,539 | 350.3 | 32,260 |
| $C_8$ Saturates | 0.1 | 8 | 0.7 | 80 |
| $C_9$ Aromatics | 49.4 | 2,566 | 272.4 | 32,742 |
| $C_{10}$ Aromatics | 1.5 | 79 | 7.4 | 993 |
| $C_{11}$ Aromatics | −0.1 | 6 | 0.5 | 74 |
| TOTAL | 100.0 | 5,198 | | 66,149 |
| Yield | | | | |
| Methane | | | | 679 |
| Ethane | | | | 500 |
| Propane | | | | 160 |
| Butane | | | | 80 |
| Benzene | 8.5 | 442 | 72.9 | 5,693 |
| Ethyl Benzene | 3.8 | 200 | 23.9 | 2,541 |
| Para Xylene 26% | 21.7 | 1,127 | 133.9 | 14,220 |
| Meta Xylene 50% | 41.7 | 2,168 | 258.6 | 27,468 |
| Ortho Xylene 24% | 20.0 | 1,040 | 126.3 | 13,413 |
| Coke 2.02 wt. % | | | | 1,395 |
| TOTAL | | | | 66,149 |

The overhead cut from the xylene column is pumped to the paraxylene recovery facility 24 where paraxylene is extracted as a finished product. The paraxylene separation is a fractionation process which comprises an adsorbent chamber through which the xylene feed and a desorbent (i.e. toluene, diethylbenzene) are passed over a fixed bed of a solid adsorbent. The desorbent and paraxylene are separated in an extraction column, whereas desorbent and raffinate are separated in a raffinate column. The adsorbed paraxylene is recovered from the adsorbent by washing it with a desorbent liquid having a boiling point different from any of the xylene aromatics. The products are separated from the desorbent by fractionation. The process arrangement simulates continuous countercurrent flow of adsorbent and liquid, without actual movement of the solid. This is accomplished with a cycle timer and valves which direct fresh feed and stripping liquid to different parts of the bed at predetermined time periods. Because of this arrangement, a single bed of adsorbent can be used and the flow of feed and products to and from the bed is continuous. The other commercially proven method for paraxylene recovery is a low-temperature crystallization which may be used in place of the adsorbent method.

Ethyl benzene, metaxylene, and orthoxylene are pumped to the xylene isomerization unit 25 where they are partially converted into small amounts of gas and benzene and into paraxylene. That stream is recycled to the stabilizer and fractionation train.

In an embodiment of an isomerization procedure a non-equilibrium mixture of xylenes and related compounds is driven toward equilibrium — which under the conditions employed may be about 25% paraxylene.

In this procedure aromatics are hydrogenated over a regenerable catalyst to the corresponding naphthene, which is isomerized and then dehydrogenated to a different aromatic isomer. The procedure, illustrated generally by unit 25, is that the mixed xylenes from the paraxylene recovery unit are mixed with hyrogen, preheated and passed through a bed of catalyst. In the catalyst bed, the xylenes are isomerized to a near equilibrium mixture of orthoxylene, metaxylene, paraxylene, and ethylbenzene. Because of side reactions, some compounds both ligher and heavier than xylenes are produced also. The reactor outlet is cooled and sent to a flash drum. Part of the gas from the flash drum is recycled to the reactor inlet. The rest of the gas is purged to fuel. The flash drum liquid is charged to the stabilizer where light hydrocarbons are removed. The bottoms are sent to the aromatics fractionation section. Table VIII sets forth typical yield estimates for the paraxylene extraction and xylene isomerization.

TABLE VIII

PARAXYLENE EXTRACTION & XYLENE ISOMERIZATION YIELDS

| Charge From | THC | Mols/Hr. TA | TO-TAL | B/D | Wt. % | Lbs. /Hr. |
|---|---|---|---|---|---|---|
| Ethyl Benzene | 100.7 | 23.9 | 124.6 | 1,041 | | 13,235 |
| Paraxylene | 120.1 | 133.9 | 254.0 | 2,138 | | 26,975 |
| Metaxylene | 280.6 | 258.6 | 539.2 | 4,520 | | 57.268 |
| Orthoxylene | 170.2 | 126.3 | 296.5 | 2,441 | | 31,488 |
| $C_9$ Paraffins | .2 | | .2 | 2 | | 26 |
| TOTAL | | | | 10,142 | 100 | 128,992 |
| Hydrogen | | | | | | 1,540 |
| TOTAL | | | | | | 120,532 |
| Yield | | | | | | |
| Methane | | | | | | 15,543 |
| Ethane | | | | | | 1,800 |
| Benzene | | | | 249 | | 3,209 |
| Toluene | | | | 230 | | 2,917 |
| Paraxylene | | | | 8,485 | 83 | 107,063 |
| TOTAL | | | | | | 130,532 |

The transalkylation, paraxylene separation and xylene isomerization processes are all commercially used and detailed information is available from several industry sources. See, for example, From Aromatics To Polyester Intermediates by Bergen et al., 1975 UOP Process Division Technology Conference, Sept.-Nov. 1975.

Table IX presents an overall typical yield estimate by weight from the extractive distillation, the thermal hydrocracking, the paraxylene isomerization and the transalkylation.

TABLE IX

WEIGHT BALANCE

| From: | Extract Dist. | THC | PX-Isom. | Trans Alky | #/Hr. |
|---|---|---|---|---|---|
| $H_2$ | | 2,898 | −1,540 | | 1,358 |
| $C_1$ | | 24,872 | 25,543 | 679 | 41,094 |
| $C_2$ | | 17,997 | 1,800 | 500 | 20,297 |
| $C_3$ | | 13,102 | | 160 | 13,262 |
| $C_4$ | | 10,127 | | 80 | 10,207 |
| $C_5$ | | 4,398 | | | 4,398 |
| $C_6/C_7$ | 2,377 | | | | 2,377 |
| Benzene | 14,189 | | | | 14,189 |
| Toluene | | | 2,917 | | 2,917 |
| Paraxylene | | | 107,063 | | 107,063 |
| Coke | | | | 1,395 | 1,395 |
| TOTAL | | | | | 218,557 |
| Fresh Naphtha Charge 20000 B/D | | | | | 218,557 |

The foregoing process design is adapted to produce a yield of 49% by weight of paraxylene (with purity greater than 99.1%) from a heavy naphtha. Based on the naphtha in the feedstock, yields of from about 40 to 60% paraxylene may be obtained. In addition, nitration grade benzene amounting to 6.5% by weight is produced plus 1.3% of toluene for a total yield of 56.8% of these aromatics.

Alternatively, benzene and toluene yields may be increased at the expense of paraxylene by altering conditions in the thermal hydrocracking reactor particularly by increasing temperature about 50° F and by reducing or eliminating flow in the transalkylation unit. The system can be readily modified to produce other aromatics. For example orthoxylene can be produced from the system disclosed by careful fractionation techniques on the xylene stream. Pipeline quality gas production can be increased by recycling paraffins to the thermal hydrocracking reactor to the extent hydrogen is available. The process of this invention can also be used to make ethane as a product from the cryogenic unit by suitable adjustment of the condensation and flash conditions.

Figure 2:
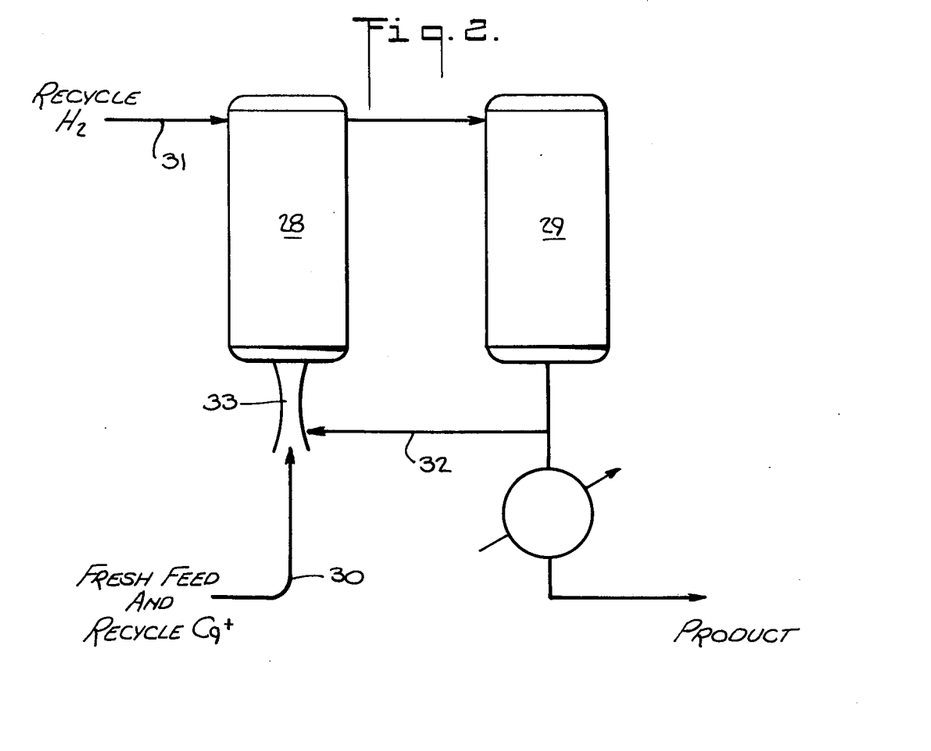
FIG. 2 illustrates the configurations of a dual reactor system for use in this invention.
Figure 3:
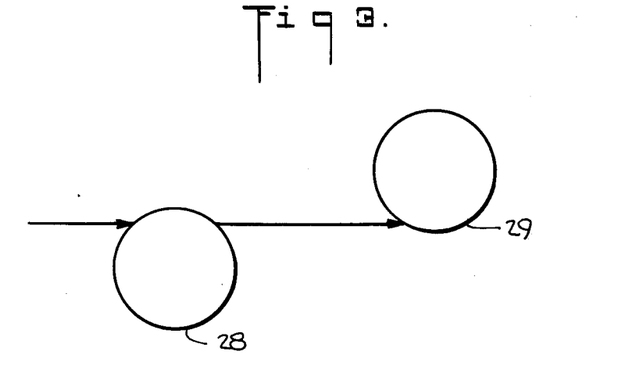
FIG. 3 is a top view of the configuration of the two reactors of FIG. 2.

In one embodiment of this invention the conventional thermal hydrocracking reactor is replaced by the dual reactor system depicted in FIGS. 2 and 3 having ceramic lined reaction surfaces. The conventional reactors used in industry are simple plug flow empty chambers which provide resistance time for the reactants and have quench points to control the exothermic reaction. In a mixed reactor the kinetic energy required to recycle, circulate, or mix the reactor is supplied by dropping the pressure of the entire feed through an inlet nozzle.

In the present invention a somewhat different reactor is designed to minimize the pressure drop of the feed and to provide better temperature control, better mixing and controlled mixing and some control over the hydrogen to feed ratio at various points in the reactor. A dual system comprising two reactors, 28 and 29, is used.

The kinetic energy required for mixing is supplied by the pumped recycle liquid 30 (which is heated and injected as a vapor) and the compressed hydrogen gas 31 external recycle circuit. The inlet temperature of each of these two streams may be precisely controlled. Some of the hot reaction products 32 from the bottom of the reactor are recycled back through the reactor by means of an eductor 33. The hydrogen/hydrocarbon ratio is lower in reactor 28 than in reactor 29 — promoting the formation of aromatics (from paraffins) and ethane in reactor 28 with additional dealkylation occurring in reactor 29. The hydrogen recycle feed stream 31 is injected into and out of the upper portion of reactor 28 to provide an eductor effect which draws up and provides mixing with the fresh feed and recycle stream 30. The temperature of the hydrogen recycle stream is used to help control the temperature in the reactors. Control is also facilitated by the use of two small reactors in place of one large unit. This arrangement eliminates the elaborate quench systems which have been used and still maintains close control over temperature and promotes the desired reactions. The tangential entry flow pattern of the streams to the reactors is illustrated in FIG. 3.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed process are considered to be within the purview and scope of this invention and the following claims.

What is claimed is:

1. The process for producing aromatic compounds from naphtha which comprises the steps of
   a. desulfurizing the naphtha;
   b. catalytically reforming the product stream of step (a) under conditions adapted to produce a substantial amount of aromatic compounds including a reforming temperature of from about 900° to 100° F and a pressure of from about 125 to 375 psig;
   c. thermally hydrocracking the product stream of step (b) at a temperature of from about 1200° to 1380° F and a pressure of from about 125 to 375 psig;
   d. separating gaseous hydrogen and lighter hydrocarbons from the product stream of step (c);
   e. recycling the hydrogen from step (d) to the feed streams of said desulfurizing, reforming and hydrocracking steps;
   f. fractionating the liquid product stream of step (c) to withdraw as products of said process a paraffin stream, a benzene-rich stream, a toluene-rich stream, and a xylene-rich stream.

2. The process of claim 1 wherein the naphtha has a boiling point range of about 212° to 374° F.

3. The process of claim 2 wherein the reforming step (b) is carried out at a catalyst temperature of about 995° to 1025° F, a liquid hourly space velocity of about .8 to 1.1 and a molar ratio of hydrogen to hydrocarbon feed of about 5 to 7.

4. The process of claim 2 wherein the thermal hydrocracking step (c) is carried out at conditions which consume less hydrogen than that produced in the reforming step.

5. The process of claim 1 wherein the thermal hydrocracking step (c) is carried out by passing the product stream of step (b) into the bottom of a first reactor and then into the top of a second reactor and maintaining adequate mixing by pumping hydrogen into the top of the first reactor, passing hydrogen and the product stream of the first reactor out of the top of said first reactor into the second reactor thereby providing a higher ratio of hydrogen to hydrocarbons in the second reactor to promote the formation of aromatics in the first reactor and dealkylation in the second reactor.

6. The process for producing xylene and a fuel gas from naphtha which comprises the steps of
   a. desulfurizing the naphtha;
   b. catalytically reforming the product stream of step (a) under conditions adapted to produce a substantial amount of aromatic compounds and which produces by-product hydrogen;
   c. thermally hydrocracking the product stream of step (b) under conditions which use less than all of the byproduct hydrogen from the reforming step;
   d. separating gaseous hydrogen and lighter hydrocarbons from the product stream of step (c);
   e. recycling the gaseous hydrogen from step (d) for use in said desulfurizing, reforming and hydrocracking steps;
   f. fractionating the liquid product stream of step (c) to withdraw a paraffin stream and a xylene — rich stream as products of said process and to remove a toluene — rich stream, and a $C_9+$ rich stream; and
   g. transalkylating the toluene-rich and $C_9+$ rich streams of step (f) and recycling the transalkylation reaction products to the fractionation step (f).

7. The process for producing paraxylene and a fuel gas from naphtha which comprises the steps of
   a. desulfurizing said naphtha;
   b. catalytically reforming the product stream of step (a) under conditions adapted to produce a substantial amount of aromatic compounds;
   c. thermally hydrocracking the product stream of step (b);
   d. separating gaseous hydrogen and lighter hydrocarbons from the product stream of step (c) to provide a liquid bottoms stream;
   e. fractionating the liquid bottom stream of step (d) to withdraw overhead a paraffin stream as product of said process from an aromatic bottoms stream;
   f. fractionating the aromatic bottoms stream from step (e) to withdraw overhead a benzene-rich stream as product of said process from a toluene-containing bottoms stream;
   g. fractionating the toluene-containing bottoms stream from step (f) to withdraw overhead a toluene-rich stream from a paraxylene-containing bottoms stream;
   h. fractionating the paraxylene-containing bottoms stream from step (g) to remove overhead a paraxylene-rich stream from a heavier aromatic bottoms stream;
   i. withdrawing paraxylene as product of said process from said paraxylene-rich stream of step (h), and the remaining liquid from said paraxylene-rich stream is recycled to step (e);
   j. fractionating the heavier aromatic bottoms bottoms stream from step (h) to remove an overhead stream which is passed together with the overhead stream from step (g) to a transalkylation reactor, and
   k. passing liquid reaction product stream from said transalkylation reactor to step (e).

8. The process of claim 7 wherein the naphtha has a boiling point range of about 212° to 374° F.

9. The process of claim 7 wherein the reforming step (b) is carried out at about 125 to 375 psig.

10. The process of claim 9 wherein the thermal hydrocracking step (c) is carried out at about the pressure of said reforming step.

11. The process of claim 9 wherein the reforming step (b) is carried out at a catalyst temperature of about 900 to 1100° F.

12. The process of claim 10 wherein the thermal hydrocracking step (c) is carried out at an outlet temperature of about 1200° to 1380° F.

13. The process of claim 7 wherein the reforming step is carried out at about 125 to 275 psig, 955° to 1025° F, a liquid hourly space velocity of 0.8 to 1.1, a molar ratio of hydrogen to hydrocarbons of 5 to 7, and the thermal hydrocracking step is carried out at about 125 to 275 psig and 1200° to 1380° F.

14. The process of claim 7 wherein the hydrocracking is carried out under conditions adapted to use less than all of the by-product hydrogen produced in the reforming step so that the entire process is in hydrogen balance.

15. The process of claim 7 wherein the thermal hydrocracking step (c) is carried out by passing the product stream of step (b) into the bottom of a first reactor and then into the top of a second reactor and maintaining adequate mixing by pumping hydrogen into the top of the first reactor, passing hydrogen and the product stream of the first reactor out of the top of said first reactor into the second reactor thereby providing a higher ratio of hydrogen to hydrocarbons in the second reactor to promote the formation of aromatics in the first reactor and dealkylation in the second reactor.

* * * * *

UNITED STATES PATENT AND TRADEMARK OFFICE
CERTIFICATE OF CORRECTION

PATENT NO. : 4,053,388
DATED : October 11, 1977
INVENTOR(S) : Angus B. Bailey

It is certified that error appears in the above–identified patent and that said Letters Patent are hereby corrected as shown below:

Column 8, line 43: Change "along" to -- alone --.

Column 12, line 57 of Table VIII: Change Total under heading Lbs./Hr from "120,532" to -- 130,532 --.

Column 13, line 12 of Table IX, under column heading Px-Isom for $C_1$: Change "25,543" to -- 15,543 --.

Column 14, line 37: Change "100°F" to -- 1100°F --.

Column 16, line 9, delete the word "bottoms" at the end of the line.

Signed and Sealed this

Fourteenth Day of February 1978

[SEAL]

Attest:

RUTH C. MASON
Attesting Officer

LUTRELLE F. PARKER
Acting Commissioner of Patents and Trademarks